United States Patent [19]

Levey et al.

[11] 4,432,249
[45] Feb. 21, 1984

[54] LIQUID SAMPLING

[76] Inventors: George Levey, 250 Tottington Rd., Bolton; Peter J. Smith, 20 Ladybridge Ave., Worsley, Manchester, both of England

[21] Appl. No.: 382,028

[22] Filed: May 26, 1982

[30] Foreign Application Priority Data

Jun. 1, 1981 [GB] United Kingdom ............... 8116629
Feb. 16, 1982 [GB] United Kingdom ............... 8204436

[51] Int. Cl.³ ............................................. G01N 1/14
[52] U.S. Cl. ................................................. 73/863.83
[58] Field of Search ............ 73/863.83, 864.34, 864.35

[56] References Cited

U.S. PATENT DOCUMENTS 4,037,472  7/1977  Gates ............................... 73/864.35
4,181,022  1/1980  Perry ............................... 73/864.35

Primary Examiner—S. Clement Swisher
Attorney, Agent, or Firm—Alan H. Levine

[57] ABSTRACT

Apparatus for obtaining samples of liquids such as raw sewage from a flow line (1) comprises a tube (2) opening into a container (4) and a tube (7) connecting between a pressure medium supply (9) and the container (4). A reservoir (8) connects with the tube (7) and can be vented. By means of the controlled operation of valves the pressure medium is used to clear the tube (2) before opening of a valve (5) a controlled volume of the pressure medium is passed to the reservoir (8) to withdraw a liquid sample into the container (4), excess sample above the level of the tube (2a) is transferred back to the flow line (1), and the tube (2) is again cleared. The valves (5, 6) do not therefore have any contact with any liquid from the line (1) during their operation.

6 Claims, 4 Drawing Figures

LIQUID SAMPLING

This invention relates to the sampling of liquids such as raw sewage sludge, crude oil, paper pulp and foods. When reference is made to liquids, it is to be understood that, although the material will behave generally as a liquid, the material may be a combination of different liquids, solids and gases, the latter probably being in solution. The invention is particularly concerned with extracting a sample from, for example, transportation pipelines, storage tanks whether pressurized or not, inter-plant pipelines, ship to shore pipelines and discharge pipelines such as bilge and cargo tank discharges into the sea.

It is known to provide apparatus for pipeline sampling, two typical devices being a rotating sphere valve and a two stroke sampler. Known samplers suffer from a number of major disadvantages, incurring the expense and disruption of requiring flange fittings on the pipeline, associated line blind valves, and special pipe sections. In operation, known samplers include seals which are under permanent pressure, and require the relative movement of mating surfaces in the presence of the pipeline liquid. They are thus very prone to seizure, high wear rates and leakage.

According to one aspect of the invention there is provided apparatus for obtaining a sample of liquid from a liquid flow line, said apparatus comprising means for containing a liquid sample, a flow path having first line means arranged to liquid flow line.

Preferably the method includes opening first valve means in the first line means after introduction of the purging fluid to the sample containing means and the first line means, and subsequently closing the first valve means after the further volume of purging fluid has been supplied, whereby the first valve means is prevented from operating in contact with liquid from the liquid flow line.

Embodiments of the present invention will now be described, by way of example, with reference to the occompanying drawings in which.

Figure 1:
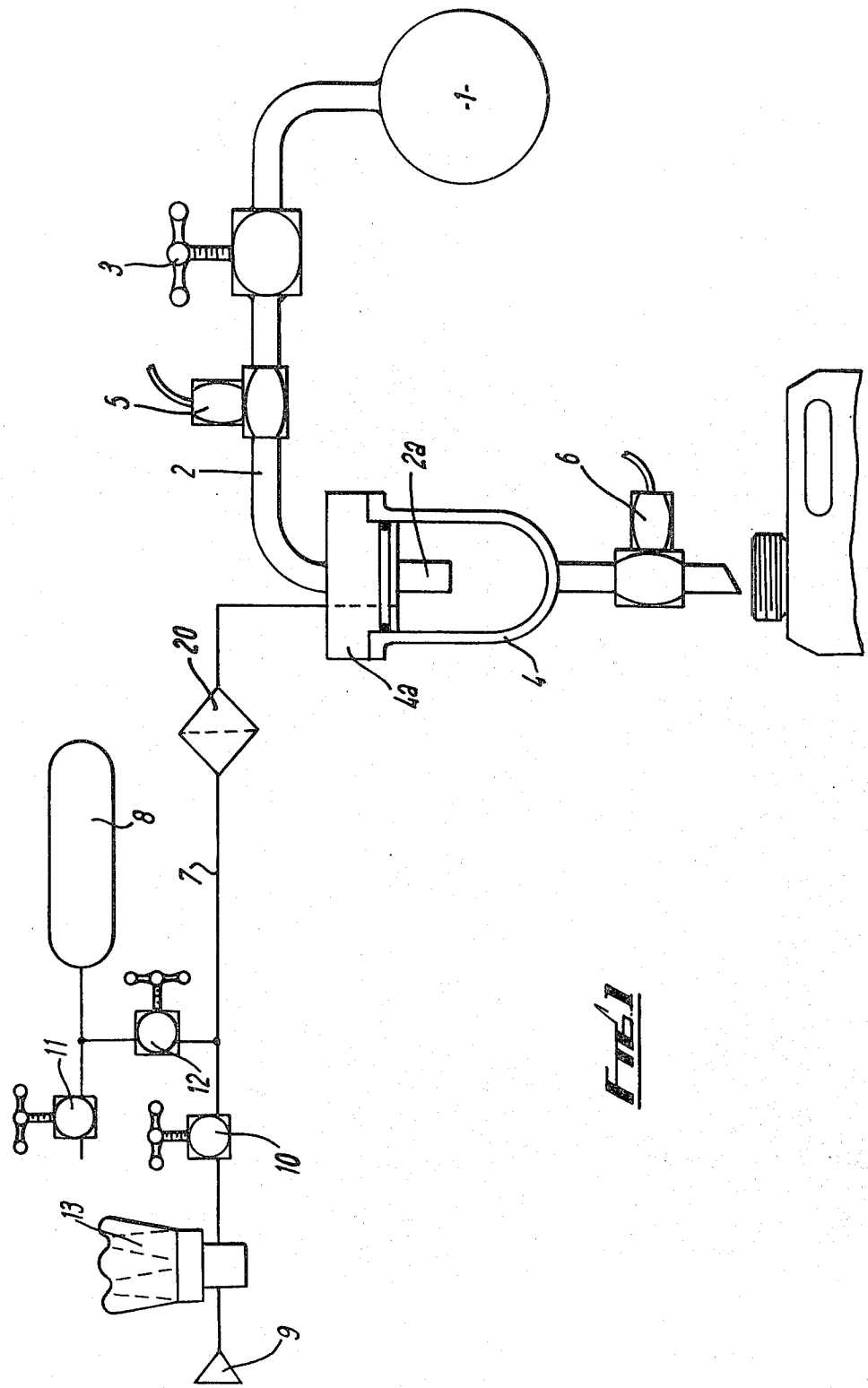
FIGS. 1, 2, 3 are diagrammatic illustrations of three embodiments.

The liquid to be sampled will be referred to as 'the medium' until a predetermined quantity thereof has been isolated, and this will be referred to as 'the sample'.

A pipeline 1 has a sampling tube 2 fixed into it, for example by welding or screwing. Note that no flanges or line blind valves are required. The sampling tube 2 preferably exits from pipeline 1 in a generally upward direction. An isolating valve 3 is placed in the sampling tube 2 and is normally open. Isolating valve 3 does not function except as a shut-off valve for replacement/repair/installation of the sampling apparatus.

Sampling chamber 4 is a pressure vessel constructed of a material suitable for such purpose. The material is also corrosion/abrasion resistant and may for example be polycarbonate, steel, or any material dictated by chemical/safety provisions relating to the medium. There is some advantage is using a transparent material for example polycarbonate or glass so that visual inspection is facilitated of the sample chamber operation, to ensure correct functioning. Also fouling by deposition or residues and interior damage may thereby be observed.

The sampling chamber 4 is preferably in the form of an inverted dome and may have a flange 4a to facilitate periodic removal of the main body portion for cleaning or replacement. Situated in the sampling tube 2 is a full bore sample intake valve 5, preferably of the diaphragm or ball type. At the base of the sampling chamber 4 is a full bore sample discharge valve 6, preferably of the diaphragm or ball type.

Entering the upper part of the sampling chamber 4 is a control tube 7, associated with which is a fluid reservoir 8, a fluid pressure source 9 and on/off valves 10, 11, 12. There may be a pressure regulating valve 13 if, for example, the pressure source is at considerably higher pressure than required for operation of the sampling apparatus.

The fluid pressure source 9, which may be gas, air, or vapour will be referred to as the purging fluid although it is important to note that this fluid has a more extensive role in operation of the sampler than just purging; it will be at a higher pressure than any normal or transient pressure which arises in the pipeline.

The operation of the apparatus will now be described in conjunction with explanations of the function to be performed by each operation.

At the commencement of sampling, the following valve conditions will prevail:

| Valve no. from drg. | Position. |
| --- | --- |
| 3 | open |
| 5 | closed |
| 6 | closed |
| 10 | closed |
| 11 | closed |
| 12 | open |

At this stage, the entire system (between valves 10 and 5) will contain purging fluid at a pressure below that available from the purging fluid source 9 or dictated by the pressure regulating valve 13 as the case may be.

Open valve 10, close valve 10. This operation, of predetermined duration, will fill the system between valve 10 and valve 5 with purging fluid.

Open valve 5. Purging fluid will discharge through valve 5 thus clearing any medium and associated debris, settled solids or the like. This discharge will continue until the entire system (from downstream of valve 10 to the junction between the pipeline and the sampling tube 2) contains purging fluid at pipeline pressure.

Close valve 12, open valve 11, close valve 11. Closing valve 12 isolates the reservoir 8, and by opening valve 11, the purging fluid in the reservoir 8 is discharged until atmospheric pressure is reached.

Open valve 12. Since the reservoir 8 is below pipeline pressure and valve 5 is still open, medium entering the sampling tube 2 from the pipeline 1 will displace purging fluid, principally from the sampling chamber 4, into the reservoir 8 until the system reverts to pipeline pressure. The volume of medium entering the system will be substantially equal to the volume of the reservoir 8, and this volume will have been determined in relation to the sampling chamber 4 such that medium will rise in the sampling chamber to a level above the bottom of the sampling tube 2, and below the bottom of the control tube 7. Note that the volume of medium which has at this stage entered the system is in excess of the volume of the sample ultimately to be obtained.

It is convenient at this stage of describing the operation to explain a further feature of the apparatus. Extending downwardly from the end of the sampling tube 2 is a volume control tube 2a; the tube 2a is, for example, screwed into the end of tube 2, and can be of any desired length, depending upon the volume of sample required, since the level in chamber 4 of the bottom of tube 2a will determine, in any given installation, the volume of the sample. Alternatively, tube 2a may be arranged to telescope so that its level can be adjusted externally of the chamber 4.

At this stage of operation, the volume of medium in the sampling apparatus will have been influenced by the pipeline pressure, and may even be varying cyclically as a result of pulsation in the pipeline.

Open valve 10. Purging fluid will flow into the sampler, thus pressurizing the free surface in the sampling chamber 4 of the medium, and this surface will fall (valve 5 is open) until the lower end of the volume control tube 2a is exposed. At this stage purging fluid will flow through the sampler and into the pipeline for a predetermined time, thus clearing the entire system from tube 2a to the pipeline connection.

Close valve 5 and then valve 10. Note that valve 5 therefore does not function in contact with the medium. At this stage, there is a sample in sample chamber 4 of a volume that has been determined solely by the geometry of the chamber and the height setting of the volume control tube 2a, and under a pressure predetermined by the pressure source 9 or regulator valve 13 as the case may be. Note that valve 12 is still open, and reservoir 8 is filled with purging fluid at its predetermined pressure.

Open valve 6. The sample of known volume is dispensed into a sample container at a known pressure via valve 6, whose discharge rate is predetermined. Note therefore that the sample container may be anything from a hand held open container to a sophisticated and fully sealed packaging machine, of either the composite or discrete package type.

After the sample has been discharged, a predetermined volume of purging fluid is discharged through valve 6.

Close valve 6. The valves are now in the following positions:

| Valve no. from drg. | Position. |
| --- | --- |
| 3 | open |
| 5 | closed |
| 6 | closed |
| 10 | closed |
| 11 | closed |
| 12 | open |

These positions correspond to the positions prior to commencement of sampling, and it will be noted that no valve has been actuated in the presence of the medium, and that the entire sampler is filled with purging fluid.

A relatively straightforward functioning of the sampler has been described but it will be clear to those skilled in the art that the basic apparatus lends itself well to more sophisticated use.

For example, in relation to a hazardous sample, it may be desirable to apply careful control of sample discharge through valve 6, and to purge into a sample container having an associated purging gas receiver. Similarly, if gaseous contamination of the purging fluid during sampling creates a hazard, then valve 11 may be discharged via a suitable filter or even into a special container.

Although only one purging source has been described, it is clearly within the scope of the present invention to use more than one purging fluid.

At one extreme all the valves may be individual and hand operated, times being determined by operator counting or stop watch. At the other extreme, multiway valves may be used, and sequencing and timing may be by automatic control. Controls may be actuated electrically, pneumatically or hydraulically, or indeed by combination of such power sources.

A restrictor 20 may be placed in the control tube between the sample chamber 4 and valve 12, the object of which is to prevent or limit accidental flow of pipeline medium downstream of restrictor 20 in the event that for example there is a leak or stuck valve in the fluid side or if an unexpected pipeline pressure rise occurs. For example, a sintered filter may be used.

Instead of separating chamber 4 at flange 4a for periodic cleaning of the lower portion of the chamber, provision may be made for in situ flushing with a cleaning liquid, for example water, by means of associated valves and pipe connections.

Tube and valve materials may be plastics or metals or combinations thereof.

As a modification, the reservoir 8 may be dispensed with entirely, together with valve 12. With such an arrangement opening valve 11 for a predetermined period or until a level of medium is detected in the sample chamber 4 (by conductive, capacitive or other level detecting means) and subsequently closing valve 11 will admit a volume of medium in excess of the volume of the sample ultimately to be obtained. Opening valve 10 will now displace excess medium back into pipeline 1.

Figure 2:
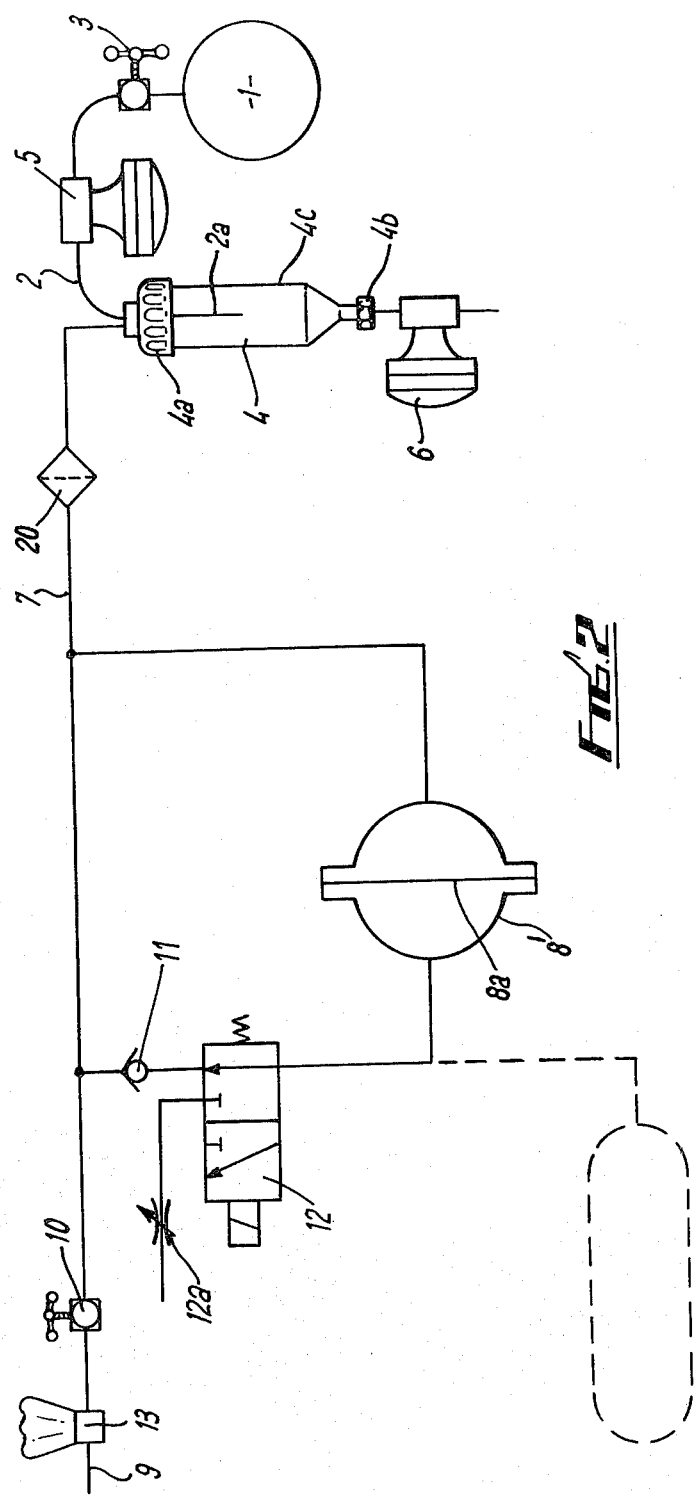

Referring now to FIG. 2, there will be described a further embodiment, wherein like references are used to denote like parts to the first embodiment. The sampling chamber 4 is preferably in the form of a partially tapered cylinder and may have connections 4a, 4b to facilitate periodic removal of the main body portion 4c for cleaning or replacement. Situated in the sampling tube 2 is a full bore sample intake valve 5, preferably of the diaphragm or ball type. At the base of the sampling chamber 4 is a full bore sample discharge valve 6, preferably of the diaphragm or ball type.

Entering the upper part of the sampling chamber 4 is a control tube 7, associated with which is a fluid reservoir 8', a fluid pressure source 9 and a 3-port 2-way valve 12. Fluid flow connections between valve 12, control tube 7 and reservoir 8' are as shown in FIG. 2, and there is a passive one-way valve 11 placed between valve 12 and control tube 7. Also, there is a restrictor or throttle valve 12a associated with the valve 12.

Reservoir 8', preferably of spherical shape, is divided equatorially, by a flexible membrane 8a, and has a total volume corresponding to but in excess of the size of sample required.

Referring briefly to the embodiment described in FIG. 1, it will be seen that the embodiment of FIG. 2 differs principally in that its static reservoir 8' has been replaced by a dynamic diaphragm reservoir, and the valves and fluid flow connections to the reservoir differ.

It may be that the fluid becomes contaminated by gases or vapours emanating from the pipeline liquid, such as to be hazardous if discharged to atmosphere from valve 11 of FIG. 1. With the arrangement of FIG.

2, it can readily be arranged that, subject only to integrity of the membrane 8a, contaminated fluid is always vented to the pipeline and only clean fluid is vented to atmosphere.

The operation of the apparatus of FIG. 2 will now be described in conjunction with explanations of the function to be performed by each operation.

At the commencement of sampling, the following valve conditions will prevail:

| Valve no. from FIG. 1. | Position. |
|---|---|
| 3 | open |
| 5 | closed |
| 6 | closed |
| 10 | closed |
| 11 | inactive |
| 12 | open to valve 11 |
| 12a | inactive |

At this stage, the entire system (between valves 10 and 5) will contain purging fluid at a pressure below that available from purging fluid source 9, and the diaphragm 8a, stressed only by its own elasticity, will be centrally situated in reservoir 8.

Open valve 10, valve 11 opens passively, close valve 10. The entire system, as far as valve 5, fills with purging fluid at supply pressure, including both sides of diaphragm 8a.

Open valve 5. Purging fluid will discharge through valve 5, thus clearing any medium and associated debris settled solids or the like from the system. As the pressure in control tube 7 drops towards line pressure, purging fluid pressure to the left of diaphragm 8a will close one-way valve 11 and progressively displace the diaphragm 8a until it is pressed against the right hand hemisphere of reservoir 8. Purging fluid flow through valve 5 ceases when the system reaches pipeline pressure.

If, as is possible but unlikely, the purging fluid pressure is less than twice the pipeline pressure, pressures across the diaphragm will equalize before full displacement of the diaphragm occurs. In such a case an additional passive reservoir of sufficient volume is connected to the left hand hemisphere of reservoir 8.

Energize valve 12 (valve 5 still open). Energizing valve 12 closes the port connected to one-way valve 11 and opens the port connected to throttle 12a. In this configuration purging fluid in the left hand hemisphere of reservoir 8 (and the additional passive reservoir if present) will vent to atmosphere in a controlled manner determined by the characteristics of throttle 12a, and the diaphragm will move across the reservoir 8. As the pressure to the right of diaphragm 8a drops medium from pipeline 1 will enter the sampling tube 2 and flow into the sampling chamber 4, progressively displacing purging fluid, until leftwards movement of the membrane 8a has been completed, and the sampling system reverts to pipeline pressure.

Except to the extent that pipeline pressure may have varied during the sampling procedure, the volume of medium entering the sampling chamber 4 will correspond to the 'swept' volume of reservoir 8. Note that medium will not completely fill sampling chamber 4.

Open valve 10 (valve 5 still open, valve 12 still energized). Purging fluid will flow into sampling chamber 4 and force medium back into the pipeline 1 until the end of volume control tube 2a is exposed. Further flow of purging fluid will discharge into the pipeline, thus purging sampling tube 2 and valves 5 and 3.

Close valve 5, then valve 10 (valve 12 still energized). Note that valve 5 therefore does not function in contact with the medium. At this stage, there is a sample in sample chamber 4 of a volume that has been determined solely by the geometry of the chamber and the level setting of the outlet of the volume control tube 2a, and under a pressure predetermined by the pressure source 9 or regulator valve 13 as the case may be. The remainder of the system is filled with purging fluid at its supply pressure.

De-energize valve 12, open valve 6. The sample of known volume is dispensed into a sample container at a known pressure via valve 6, whose discharge rate is predetermined. Note therefore that the sample container may be anything from a hand held open container to a sophisticated and fully sealed packaging machine, of either the composite or discrete package type. De-energizing of valve 12 will re-open the left hand side of the reservoir 8 to the control tube 7 via one-way valve 11. After the sample has been discharged a predetermined volume of purging fluid will flow through valve 6, thus purging it.

Close valve 6. The valves are now in the following positions:

| Valve no. from FIG. 1. | Position. |
|---|---|
| 3 | open |
| 5 | closed |
| 6 | closed |
| 10 | closed |
| 11 | inactive |
| 12 | open to valve 11 |
| 12a | inactive. |

These positions correspond to the positions prior to commencement of sampling, and it will be noted that no valve has been actuated in the presence of the medium, and that the entire sampler is filled with purging fluid. Also, note that the membrane has returned to its equatorial position.

Figure 3:
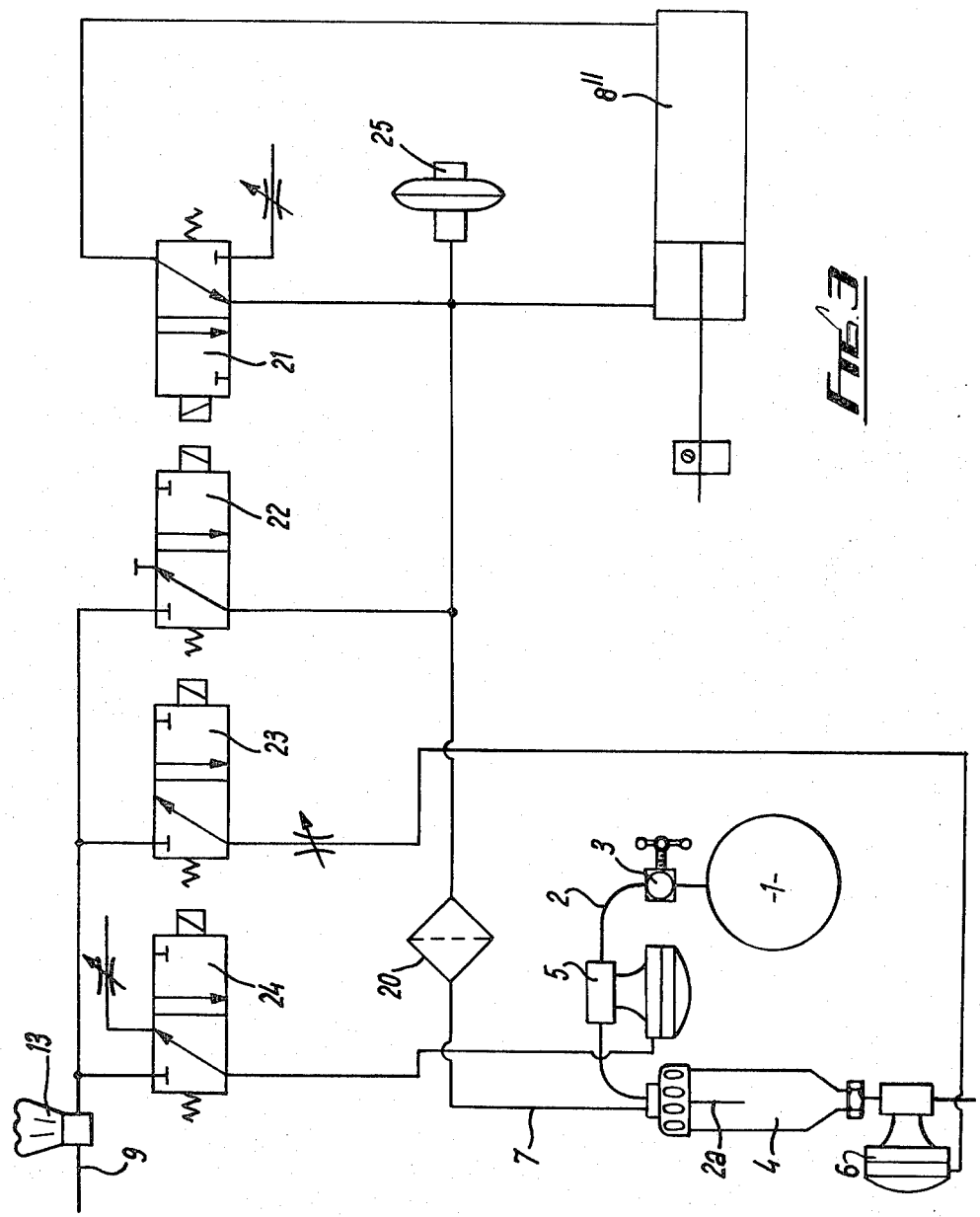

Reference will now be made to FIG. 3 of the drawings accompanying the present application. Purging and medium flows are broadly similar to the embodiment already described, and the present embodiment is principally concerned with describing one method of operating and interlocking the control of the various valves. Prior to commencing a sampling cycle, the following conditions prevail:

| All valves de-energized. | |
|---|---|
| Valve 21 | open |
| Valves 22, 23, 24 | closed |
| Valve 5 | closed |
| Valve 6 | closed |

Valves 5 and 6 are pneumatically actuated diaphragm valves operated by opening valves 24 and 23 respectively to purging fluid. A reservoir 8″ comprises a piston and cylinder assembly having an adjustable stop to control the stroke of the piston.

Pressure switch 25 has contacts which are normally open, and which are set to close in response to exposure to a pressure corresponding to the minimum acceptable purging fluid pressure for a given installation.

The sequence of operation is as follows:

Check Pressure switch 25 open. If purging fluid has leaked into the system to any significant extent, then pressure switch 25 will have closed. Also, if the previous sampling cycle has failed to discharge the sample through valve 6, the sampling system will have remained at or near purging pressure and the switch will have remained closed.

If this check reveals that pressure switch 25 is closed, sampling sequence is aborted and an alarm signal is given.

Open valve 22. This will pressurize the sample chamber 4, close pressure switch 25 and pressurize the reservoir 8" from both sides of the piston. The differential thrust on the piston arising from the piston rod cross section will ensure that piston is displaced fully to the left. Note that if the purge pressure is below the predetermined minimum acceptable, then the pressure switch 25 will not close and abort and alarm will result.

Close valve 22. This isolates the sampling system from the purge pressure source. A delay in the sequence occurs at this stage, and the condition of pressure switch 25 is monitored. If there is a leak of significance, pressure switch 25 will open and abort and alarm will result.

Open valve 24. Valve 5 is thus pneumatically opened, and sampling tube 2 is purged, since the system has already been pressurized to purge fluid pressure by the earlier opening of valve 22.

Energize valve 21. This vents the right hand end of reservoir cylinder 8" to atmosphere via a restrictor or throttle valve, thus enabling an intake of medium at a controlled rate and of volume equal to the swept volume of reservoir cylinder 8"; this in turn is controlled by means of an adjustable stop on the associated piston rod.

Open valve 22. This causes blowback of excess medium until correct sample height is achieved in sampling chamber 4, and subsequent purging.

Close valve 24. (Valve 22 still open). Actuation of valve 24 effects the closure of valve 5 at a rate governed by a suitable restrictor, thus achieving a progressive and controlled closure of the diaphragm of valve 5 whilst purging fluid continues to flow across it and thence into the pipeline 1.

Close valve 22. De-energizing valve 22 after valve 5 has closed ensures that the system is again at purge pressure.

De-energize valve 21. By re-connecting the right hand end of the reservoir cylinder 8" to the system, the piston is returned to its initial position, and the system pressure reduced to an extent corresponding to the portion of the full stroke actually used.

Energize valve 23. Purge pressure is applied to the pneumatically actuated valve 6 via a restrictor which thus opens slowly giving a controlled discharge of the sample.

De-energize valve 23. Sequence completed.

Figure 4:
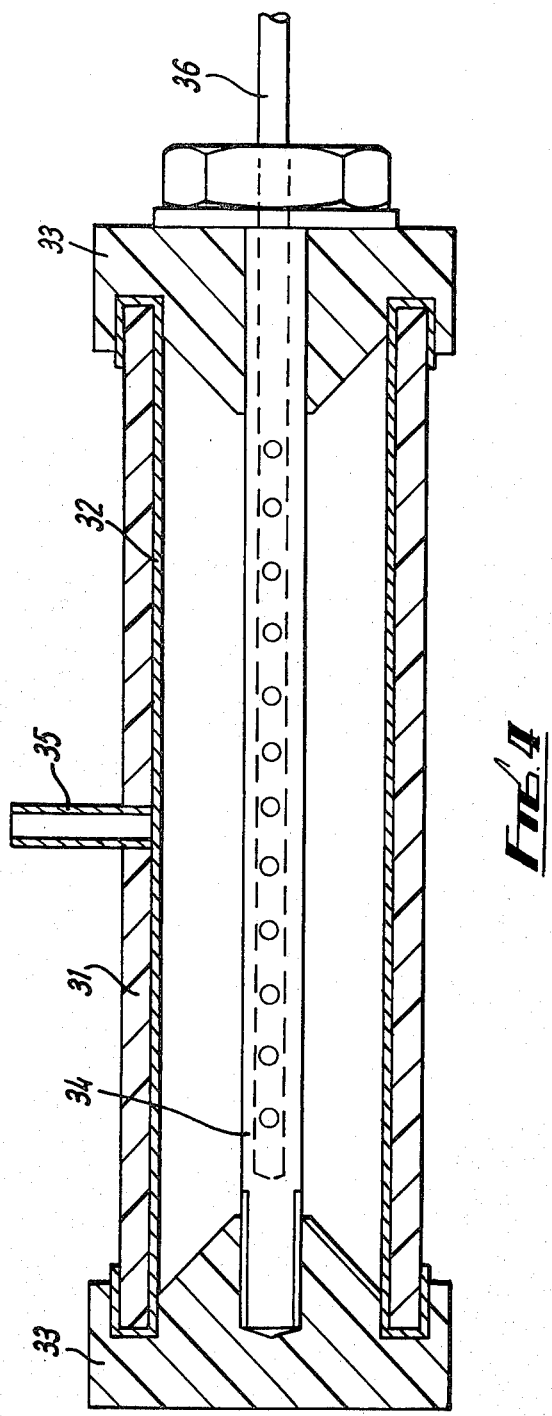
FIG. 4 is a diagrammatic illustration of an alternative reser voir.

The spherical reservoir of the embodiment described in relation to FIG. 2 has the advantage over that of the cylinder of FIG. 3 that there are no moving parts (other than the diaphragm). However, spherical pressure vessels are expensive and inconvenient in small quantity production, and an alternative form of reservoir may be preferred, as now described with reference to FIG. 4.

A length of standard p.v.c. pressure pipe 31 is cut diametrically to form a cylinder. A length 32 of flexible tube of similar diameter to that of cylinder 31 is placed inside the cylinder. This tube may for example be rubber.

Two end pieces 33 e.g. of turned p.v.c. are positioned in the cylinder 31, with the ends of the tube 32 sandwiched therebetween.

A hollow drawbolt 34 clamps the assembly together. Purge fluid connections 35, 36 complete the reservoir.

It will readily be seen that suitable connections of lines 35, 36 will enable this reservoir to be applied to the embodiments already described.

We claim:

1. Apparatus for obtaining a sample of liquid from a liquid flow line, said apparatus comprising means for containing a liquid sample, a flow path having first line means with a first valve therein arranged to selectively provide communication between the sample containing means and the liquid flow line, and second line means for selectively delivering a purging fluid, at a pressure higher than the pressure in the liquid flow line, from a supply to the sample containing means and the first line means, means for controlling purging fluid so that said first valve is prevented from operating in contact with liquid from the liquid flow line.

2. Apparatus according to claim 1, including a reservoir for selectively receiving a volume of the purging fluid from the flow path, and means for releasing said volume of the purging fluid from the reservoir to atmosphere.

3. Apparatus according to claim 2, wherein the reservoir comprises a container in which two chambers are defined by a diaphragm, the releasing means being operatively connected with one of the chambers and the other of the chambers being connected in the second line means.

4. Apparatus according to claim 2, wherein the reservoir comprises a piston and cylinder assembly, the releasing means being operatively connected with one side of the piston and the other side of the piston being connected in the second line means.

5. A method of obtaining a sample of liquid from a liquid flow line, said method comprising introducing a purging fluid at a pressure higher than the pressure in the liquid flow line, through second line means, to sample containing means and first line means, causing a volume of sample liquid from the flow line to enter the sample containing means, and supplying a further volume of purging fluid to the sample containing means whereby both purging fluid and sample liquid in excess of a desired amount are discharged into the liquid flow line, opening first valve means in the first line means after introduction of the purging fluid to the sample containing means and the first line means, and subsequently closing the first valve means after the further volume of purging fluid has been supplied, whereby the first valve means is prevented from operating in contact with liquid from the liquid flow line.

6. A method according to claim 5, wherein a controlled volume of the purging fluid first introduced to the sample containing means and the first line means is released to cause a substantially corresponding volume of sample liquid to enter the sample containing means.

* * * * *